(12) United States Patent
Glickman et al.

(10) Patent No.: US 9,305,059 B1
(45) Date of Patent: Apr. 5, 2016

(54) METHODS, SYSTEMS, AND COMPUTER READABLE MEDIA FOR DYNAMICALLY SELECTING QUESTIONS TO BE PRESENTED IN A SURVEY

(75) Inventors: Seth Glickman, Chapel Hill, NC (US); Kevin Schulman, Chapel Hill, NC (US); Sara Frances Heard, Durham, NC (US); Amanda Paige Norman Wilkins, Apex, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 514 days.

(21) Appl. No.: 13/530,042

(22) Filed: Jun. 21, 2012

Related U.S. Application Data

(60) Provisional application No. 61/499,508, filed on Jun. 21, 2011.

(51) Int. Cl.
*G06F 7/00* (2006.01)
*G06F 17/00* (2006.01)
*G06F 17/30* (2006.01)

(52) U.S. Cl.
CPC .............................. *G06F 17/30522* (2013.01)

(58) Field of Classification Search
CPC .......... G06F 17/3053; G06F 17/30522; G06F 17/30554; G06F 17/30643
USPC ..................... 707/723, 728; 706/46; 715/243; 705/1.1, 10
See application file for complete search history.

(56) References Cited

U.S. PATENT DOCUMENTS

| | | | |
|---|---|---|---|
| 7,181,438 B1 * | 2/2007 | Szabo | |
| 7,330,823 B1 * | 2/2008 | DeRosier et al. | 434/322 |
| 7,581,176 B2 * | 8/2009 | Wilson | 715/243 |
| 7,818,315 B2 * | 10/2010 | Cucerzan et al. | 707/723 |
| 8,239,227 B2 * | 8/2012 | Megiddo et al. | 705/7.11 |
| 2003/0050928 A1 * | 3/2003 | Hays | 707/6 |
| 2005/0197988 A1 * | 9/2005 | Bublitz | 706/46 |
| 2006/0281987 A1 * | 12/2006 | Bartesaghi et al. | 600/410 |
| 2008/0255862 A1 * | 10/2008 | Bailey et al. | 705/1 |
| 2010/0145715 A1 * | 6/2010 | Cohen | 705/1.1 |
| 2012/0330946 A1 * | 12/2012 | Arredondo et al. | 707/728 |

OTHER PUBLICATIONS

Barr et al., "Using public reports of patient satisfaction for hospital quality improvement," Health Serv Res., 41, pp. 663-682 (2006).
Barr et al., "Public reporting of hospital patient satisfaction: the Rhode Island experience," Health Care Financ Rev., 23, pp. 51-70 (2002).

(Continued)

*Primary Examiner* — Susan Chen
(74) *Attorney, Agent, or Firm* — Jenkins, Wilson, Taylor & Hunt, P.A.

(57) ABSTRACT

According to one aspect, the subject matter described herein includes a method for dynamically selecting questions to be presented in a survey. The method includes providing for assignment of priorities to potential survey questions. The method further includes determining a selection probability for each question based on the assigned priorities. The method further includes storing questions in a database embodied in a non-transitory computer readable medium. The method further includes dynamically selecting, from the database and based on the selection probabilities, questions to be included in surveys to be presented to a plurality of individuals such that different individuals are presented with different sets of questions.

19 Claims, 17 Drawing Sheets

(56) References Cited

OTHER PUBLICATIONS

Beach et al., "Is the quality of the patient-provider relationship associated with better adherence and health outcomes for patients with HIV?" J Gen Intern Med, 21(6), pp. 661-665 (2006).
Bhatt et al., "Utilization of early invasive management strategies for high-risk patients with non-ST-segment elevation acute coronary syndromes: results from the CRUSADE Quality Improvement Initiative," JAMA, 292, pp. 2096-2104 (2004).
Boersma et al., "Predictors of outcome in patients with acute coronary syndromes without persistent ST-segment elevation: results from an international trial of 9461 patients," Circulation, 101, pp. 2557-2567 (2000).
Boulding et al., "Relationship Between Patient Satisfaction with Inpatient Care and Hospital Readmission Within 30 Days," American Journal of Managed Care (2010).
Boulding et al., "The quality double whammy," Marketing Science, 18(4), pp. 463-484 (1999).
Boulding et al., "A dynamic process model of service quality: from expectations to behavioral interventions," J Mark Res., 30(1), pp. 7-27 (1993).
Brody et al., "Patient perception of involvement in medical care: relationship to illness attitudes and outcomes," J Gen Intern Med, 4(6), pp. 506-511 (1989).
Centers for Medicare & Medicaid Services. HCAHPS facts, http://www.hcahpsonline.org/facts.aspx (May 2012).
Chow "Tests of equality between sets of coeffcients in two linear regressions," Econometrica, 28, pp. 591-605 (Jul. 1960).
Covinsky et al., "The relation between health status changes and patient satisfaction in older hospitalized medical patients," J Gen Intern Med., 13(4), pp. 223-227 (1998).
Curtis et al., "Early and long-term outcomes of heart failure in elderly persons, 2001-2005," Arch Intern Med, 68(22), pp. 2481-2488 (2008).
Darby et al., "Development and evaluation of the CAHPS hospital survey," Health Serv Res., 40(6 Pt 2), pp. 1973-1976 (2005).
Fonarow et al., "Heart failure performance measures and outcomes: real or illusory gains," JAMA, 302(7), pp. 792-794 (2009).
Fonarow et al., "Association between performance measures and clinical outcomes for patients hospitalized with heart failure," JAMA, 297(1), pp. 61-70 (2007).
Glickman et al., "Patient Satisfaction and its Relationship with Clinical Quality and Inpatient Mortality in Acute Myocardial Infarction," Journal of the American Heart Association, Circulation Cardiovascular Quality and Outcomes, vol. 3, pp. 188-195 (2010).
Glickman et al., "Pay for performance, quality of care, and outcomes in acute myocardial infarction," JAMA, 297(21), pp. 2373-2380 (2007).
Goldstein et al., "Measuring hospital care from the patients' perspective: an overview of the CAHPS Hospital Survey development process," Health Serv Res., 40: pp. 1977-1995 (2005).
Greenwald et al., "The hospital discharge: a review of a high risk care transition with highlights of a reengineered discharge process," J Patient Saf., 3(2), pp. 97-106 (2007).
HCAHPS (Hospital Consumer Assessment of Healthcare Providers and Systems) facts. Centers for Medicare and Medicaid Services Web site. Available at: http://www.cms.hhs.gov/apps/media/press/factsheet.asp?Counter 3007&intNumPerPage 10&checkDate &checkKey &srch Type 1&numDays 3500&srchOpt 0&srchData &keywordType All&chkNewsType 6&intPage &showAll &pYear &year &desc false& cboOrder date. Updated Mar. 28, 2008 (Accessed Mar. 23, 2009).
Hoekstra et al., "Improving the care of patients with non-ST-elevation acute coronary syndromes in the emergency department: the CRUSADE initiative," Acad Emerg Med., 9, pp. 1146-1155 (2002).
Institute of Medicine, "Crossing the Quality Chasm: A New Health System for the 21st Century," Washington, DC: National Academy Press (2001).
Jack et al., "A reengineered hospital discharge program to decrease rehospitalization: a randomized trial," Ann Intern Med., 150(3), pp. 178-187 (2009).
Jaipaul et al., "Do hospitals with lower mortality have higher patient satisfaction? A regional analysis of patients with medical diagnoses," Am J Med Qual., 18, pp. 59-65 (2003).
Jencks et al., "Rehospitalizations among patients in the Medicare fee-for-service program," N Engl J Med., 360(14), pp. 1418-1428 (2009).
Jha et al., "Patients' perceptions of hospital care in the United States," N Eng J Med., 359, pp. 1921-1931 (2008).
Krumholz et al., "Measuring performance for treating heart attacks and heart failure: the case for outcomes measurement," Health Aff (Millwood), 26(1), pp. 75-85 (2007).
Kurtzman et al., "The current state of nursing performance measurement, public reporting, and value-based purchasing," Policy Polit Nurs Pract., 9, pp. 181-191 (2008).
Kurtzman et al., "Measuring the contribution of nursing to quality, patient safety, and health care outcomes," Policy Polit Nurs Pract., 8, pp. 20-36 (2007).
Needleman et al., "Performance measurement of nursing care: state of the science and the current consensus," Med Care Res Rev., 64(2 Suppl), pp. 10S-43S (2007).
Needleman et al., "Nursestaffing levels and the quality of care in hospitals," N Engl J Med., 346, pp. 1715-1722 (2002).
Peterson et al., "Association between hospital process performance and outcomes among patients with acute coronary syndromes," JAMA, 295, pp. 1912-1920 (2006).
Premier Inc. Centers for Medicare & Medicaid Services (CMS)/Premier Hospital Quality Improvement Demonstration (HQID) project: findings from year two. http://www.premierinc.com/quality-safety/tools-services/p4p/hqi-whitepaper-year2.pdf (May 2007).
Ross et al., "Statistical models and patient predictors of readmission for heart failure: a systematic review," Arch Intern Med., 168, pp. 1371-1386 (2008).
Shah et al., "The impact of for-profit hospital status on the care and outcomes of patients with non-ST-segment elevation myocardial infarction: results from the CRUSADE Initiative," J Am Coil Cardiol., 50, pp. 1462-1468.
Shepperd et al., "Discharge planning from hospital to home," Cochrane Database Syst Rev., vol. 1:CD000313.
Staman et al., "Quality improvement tools designed to improve adherence to ACC/AHA guidelines for the care of patients with non-ST-segment acute coronary syndromes: the CRUSADE quality improvement initiative," Crit Pathw Cardiol., 2, pp. 34-40 (2003).
Stewart, "Effective physician-patient communication and health outcomes: a review," CMAJ, 152, pp. 1423-1433.
White, "Measuring Patient Satisfaction: How to Do it and Why to Bother," Family Practice Management, pp. 40-44 (Jan. 1999).
"A path to bundled payment around a rehospitalization," In: Report to the Congress: Reforming the Delivery System, Washington, DC: Medicare Payment Advisory Commission, pp. 83-103 (Jun. 2005).

\* cited by examiner

| Category A | Category B | Category C |
|---|---|---|
| Q1 | Q1 | Q1 |
| Q2 | Q2 | Q2 |
| Q3 | Q3 | Q3 |
| Q4 | Q4 | Q4 |
| Q5 | Q5 | Q5 |
| ... | ... | ... |

400

→ Manager assigns a total of 100 points across all categories (k) based on their priorities. In this example there are 3 categories and 5 questions per category but there is no limit to the number of potential categories or questions

| Category A = 30 | Category B = 60 | Category C = 10 |
|---|---|---|
| Q1 | Q1 | Q1 |
| Q2 | Q2 | Q2 |
| Q3 | Q3 | Q3 |
| Q4 | Q4 | Q4 |
| Q5 | Q5 | Q5 |
| ... | ... | ... |

402

In this case the manager felt category B was the most important and assigned 60% weighting, followed by Category A (30 points) and Category C (10 points).

| Category A = 30 | Category B = 60 | Category C = 10 | ... |
|---|---|---|---|
| Q1 | Q1 | Q1 | |
| Q2 | Q2 | Q2 | |
| Q3 | Q3 | Q3 | |
| Q4 | Q4 | Q4 | |
| Q5 | Q5 | Q5 | |
| ... | ... | ... | |

Manager assigns a total of 100 points across the questions (j) within each category based on their priorities. The manager also has the opportunity to add their own questions.

406

| Category A = 30 | Category B = 60 | Category C = 10 | ... |
|---|---|---|---|
| Q1 = 20 | Q1 = 40 | Q1 = 0 | |
| Q2 = 20 | Q2 = 20 | Q2 = 0 | |
| Q3 = 20 | Q3 = 10 | Q3 = 0 | |
| Q4 = 20 | Q4 = 10 | Q4 = 50 | |
| Q5 = 20 | Q5 = 20 | Q5 = 50 | |
| ... | ... | ... | |

FIG. 4B

| Category A = 30 | Category B = 60 | Category C = 10 |
|---|---|---|
| Q1 = 20 | Q1 = 40 | Q1 = 0 |
| Q2 = 20 | Q2 = 20 | Q2 = 0 |
| Q3 = 20 | Q3 = 10 | Q3 = 0 |
| Q4 = 20 | Q4 = 10 | Q4 = 50 |
| Q5 = 20 | Q5 = 20 | Q5 = 50 |
| ... | ... | ... |

408

The sampling probability weights for each individual question are calculated by category weight (j) * question weight (k)

→

| Category A | Category B = 60 | Category C = 10 |
|---|---|---|
| Q1 = .3*.2=.06 | Q1 = .6*.4=.24 | Q1 = .1*0=0 |
| Q2 = .3*.2=.06 | Q2 = .6*.2=.12 | Q2 = .1*0=0 |
| Q3 = .3*.2=.06 | Q3 = .6*.1=.06 | Q3 = .1*0=0 |
| Q4 = .3*.2=.06 | Q4 = .6*.1=.06 | Q4 = .1*.5=.05 |
| Q5 = .3*.2=.06 | Q5 = .6*.2=.12 | Q5 = .1*.05=.05 |
| ... | ... | ... |

410

The sum of sampling probability weights for all questions will total to 1.

FIG. 4C

Question weighting on initial sample of surveys (1-50)

| Cat A | Cat B | Cat C |
|---|---|---|
| Q1=.06 | Q1=.24 | Q1=0 |
| Q2=.06 | Q2=.12 | Q2=0 |
| Q3=.06 | Q3=.06 | Q3=0 |
| Q4=.06 | Q4=.06 | Q4=.05 |
| Q5=.06 | Q5=.12 | Q5=.05 |

→

Question weighting next survey #51

| Cat A | Cat B | Cat C |
|---|---|---|
| Q1=.08 | Q1=.05 | Q1=0 |
| Q2=.10 | Q2=.25 | Q2=0 |
| Q3=.04 | Q3=.02 | Q3=0 |
| Q4=.02 | Q4=.11 | Q4=.10 |
| Q5=.08 | Q5=.20 | Q5=.05 |

In this hypothetical scenario the weights are adjusted for survey #51. Q1 (B) was initially the highest priority question – among the initial respondents the variance of the response was low, indicating a high degree of confidence in the true answer. Therefore the question was de-weighted from 0.24 to 0.05. In contrast, Q2(B) initially received a moderate weighting of 0.12. In this scenario the answers among the initial respondents were highly variable. Since this question is important and the true answer is still unclear the weighting for this question increased significantly from 0.12 to 0.25.

METHODS, SYSTEMS, AND COMPUTER READABLE MEDIA FOR DYNAMICALLY SELECTING QUESTIONS TO BE PRESENTED IN A SURVEY

PRIORITY CLAIM

This application claims the benefit of U.S. Provisional Patent Application Ser. No. 61/499,508, filed Jun. 21, 2011; the disclosure of which is incorporated herein by reference in its entirety.

TECHNICAL FIELD

The subject matter described herein relates to survey administration in healthcare and non-healthcare settings. More specifically, the subject matter relates to methods, systems, and computer readable media for dynamically selecting questions to be presented in a survey. The subject matter described herein also relates to automatically updating survey generation based on answers to questions in prior surveys.

BACKGROUND

Customer satisfaction surveys are an important way for an organization to measure the quality of services they provide, and, in healthcare, for hospitals and physicians to measure quality of care provided to patients. Increasingly, patient satisfaction is being tied to reimbursement for clinical services by federal agencies like the Centers for Medicare and Medicaid Services (CMS) and private insurance companies. Current patient survey approaches have significant limitations. Most existing patient surveys are overly long (30 questions or more) and delivered via antiquated means, long after the services are rendered. This results in low patient response rates, limiting statistical validity and generalizability of results. The existing survey development process is also not optimal. Surveys do not reflect fresh learnings; they are static and do not automatically update based on answers of prior respondents. They also do not reflect managers' intimate knowledge of their unique organizations.

Accordingly, a need exists for methods, systems, and computer readable media for dynamically selecting questions presented in a survey.

SUMMARY

According to one aspect, the subject matter described herein includes a method for dynamically selecting questions to be presented in a survey. The method includes providing for assignment of priorities to potential survey questions. The method further includes determining a selection probability for each question based on the assigned priorities. The method further includes storing questions in a database embodied in a non-transitory computer readable medium. The method further includes dynamically selecting, from the database and based on the selection probabilities, questions to be included in surveys to be presented to a plurality of individuals such that different individuals are presented with different sets of questions.

According to another aspect, the subject matter described herein includes a system for dynamically selecting questions presented in a survey. The system includes a questions database including a plurality of questions stored in a non-transitory computer readable medium. The system also includes a priority assignment module providing for assignment of priorities to the questions. The system further includes a selection probability determination module for determining a selection probability for each of the potential questions based on the assigned priorities. The system further includes a question selection module for dynamically selecting, from the questions database and based on the selection probabilities, questions to be included in the survey to be presented to each of the plurality of individuals such that different individuals are presented with different questions.

As used herein, the term "module" refers to software in combination with hardware (such as a processor) and/or firmware for implementing features described herein.

As will be described in more detail below, user interfaces may be provided for a manager or administrator to assign priorities to survey questions and categories for survey questions. The terms "manager" and "administrator" are used herein to refer to the individual who assigns priorities to questions and are not limited to an individual with a particular title within an organization. The term "priority" is intended to refer to an indication of relative weight or importance assigned to a question.

The subject matter described herein can be implemented in software in combination with hardware and/or firmware. For example, the subject matter described herein may be implemented in software executed by one or more processors. In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 4A is a diagram illustrating the assignment of priorities to categories according to an embodiment of the subject matter described herein;

FIG. 4B is a diagram illustrating the assignment of priorities to questions within categories according to an embodiment of the subject matter described herein;

FIG. 4C is a diagram illustrating the determination of selection probabilities for questions according to an embodiment of the subject matter described herein;

FIG. 4E is a diagram illustrating the dynamic updating of selection probabilities according to an embodiment of the subject matter described herein;

FIG. 7C is a computer screen shot of an interface for manipulating relative weights assigned to questions according to an embodiment of the subject matter described herein;

FIG. 7D is a computer screen shot illustrating the results of manipulating or changing the weight assigned to one of the questions in the interface illustrated in FIG. 7C according to an embodiment of the subject matter described herein;

DETAILED DESCRIPTION

Figure 1:
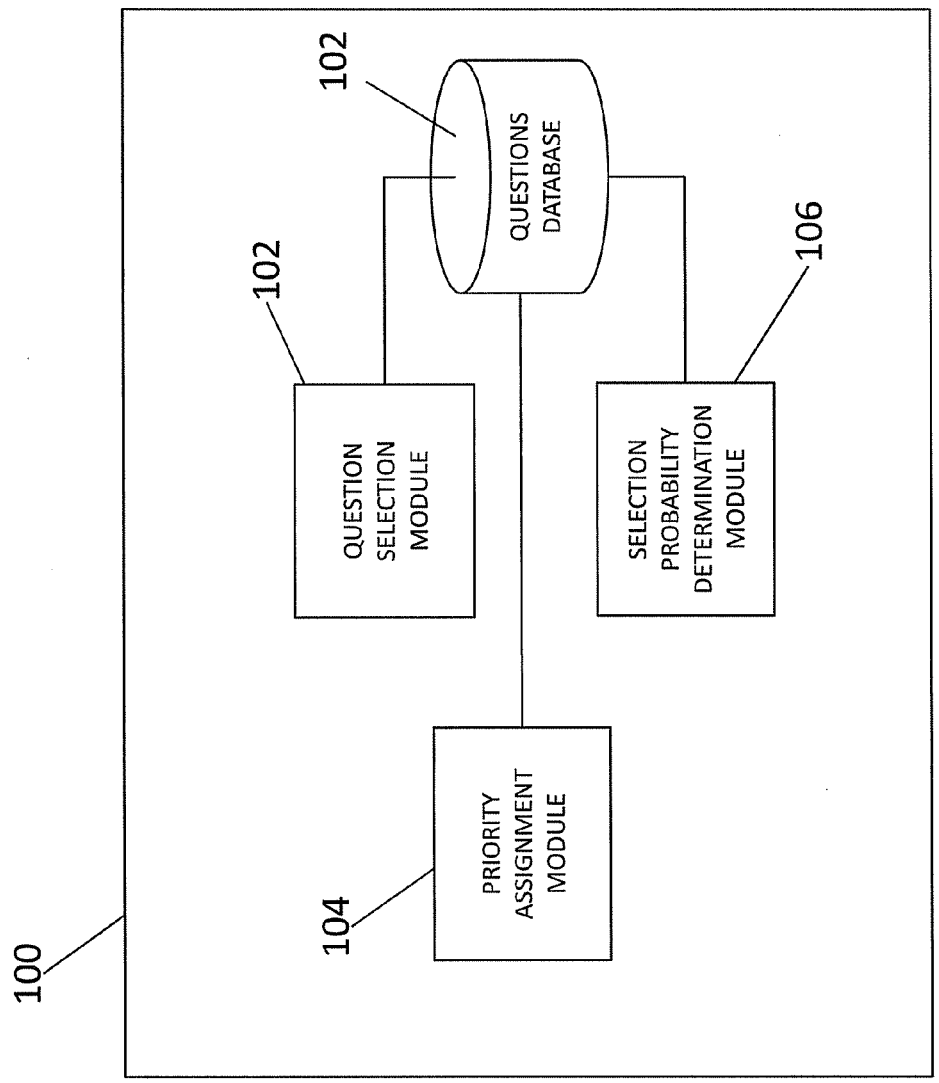
FIG. 1 is a block diagram of a system for dynamically selecting questions to be presented in a survey according to an embodiment of the subject matter described herein.

Methods, systems, and computer readable media for dynamically selecting questions presented in a survey are provided. FIG. 1 is a block diagram of an exemplary system for dynamically selecting questions to be presented in a survey in accordance with embodiments of the subject matter described herein. Referring to FIG. 1, system 100 includes a questions database 102 that stores a pool of questions to potentially be presented to users. The pool of questions may pertain to any suitable topic or industry, including healthcare, hospitality, retail, restaurants, etc. The questions may also include questions unrelated to a consumer-supplier relationship, such as questions relating to political poling. The questions may be selected by an administrator of an establishment who desires to learn how users perceive the quality of the establishment. System 100 further includes a priority assignment module 104 that allows an administrator to assign priorities to the set or pool of potential questions. Priorities may be assigned before or after the questions are stored in database 102. Priority assignment module 104 may allow the administrator to place questions in categories concerning different areas for which survey data is desired to be collected. Priority assignment module 104 may further allow the administrator to set priorities for each category and priorities for individual questions within each category. In one embodiment, priority assignment module 104 may be configured to provide the administrator with a manipulable graphical depiction of priority assigned to the categories, so that the administrator can manipulate the graphical depiction to change or assign priorities to the categories. Priority assignment module 104 may also be configured to provide the administrator with a manipulable graphical depiction of priorities assigned to questions so that the administrator can manipulate the graphical depiction to change or assign priorities to the individual questions.

System 100 further includes a selection probability determination module 106 for determining a selection probability for each question based on priorities assigned by priority assignment module 104. Selection probability determination module 106 may also dynamically update the selection probability for a given question based on user responses received in surveys. For example, if a question is always answered the same way or the answer to a question converges to a particular value over time, selection probability determination module 106 may assign a lower selection probability to that question. System 100 further includes question selection module 108 that dynamically selects questions from questions database 102 to be presented to users in a survey based on the selection probabilities. Question selection module 108 may select questions from the categories according to the priorities assigned to the categories to be presented to a user in a survey. A second user may receive a different set of questions than the first user based on the selection probabilities. Questions may be presented to users via any convenient method. For example, for a healthcare facility, users may provide an email address at registration, and question selection module 108 may present questions to each user after being discharged.

In one embodiment, selection probability determination module 106 calculates the selection probability for each question based on the priority assigned to each question and the category in which the question falls. In another embodiment, priority assignment module 104 may allow the administrator to assign priorities to each question, and priority determination module 106 may assign the selection probability for each question to be the priority assigned by the administrator.

Figure 2:
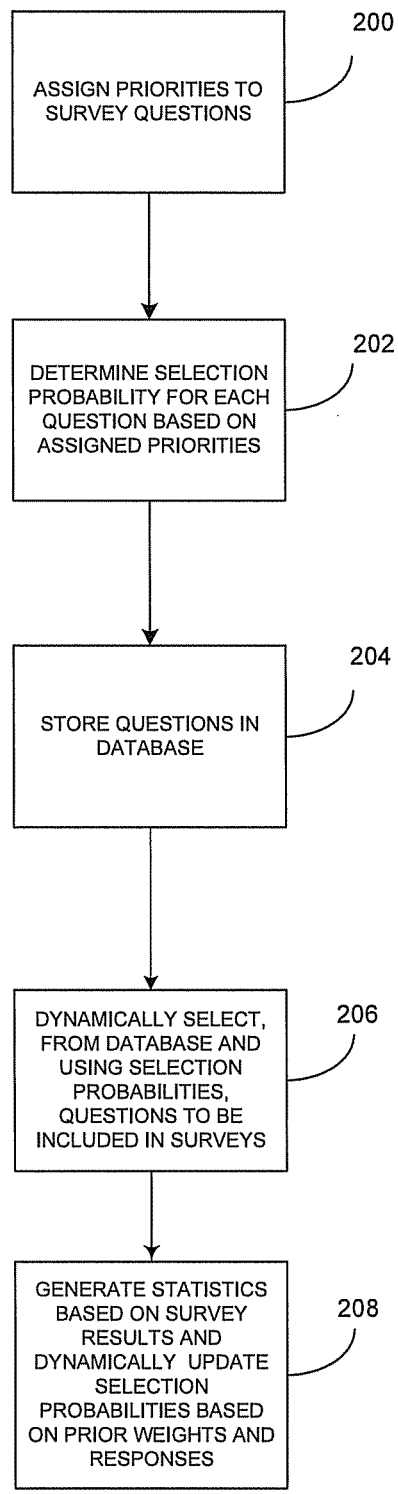
FIG. 2 is a flow chart illustrating exemplary overall steps for dynamically selecting questions to be presented in a survey according to an embodiment of the subject matter described herein.

FIG. 2 is a flow chart illustrating exemplary overall steps for dynamically selecting questions to be presented in a survey according to an embodiment of the subject matter described herein. Referring to FIG. 2, in step 200, the system provides for assignments of survey questions.

In step 202, a selection probability is determined for each question based on the assigned priorities. In one example, the selection probability may be based on the priority assigned to the category and the priority assigned to each question. In another example, the selection probability may be assigned based on the priority assigned to questions alone, if all questions are in the same category. The term "selection probability" refers to an indicator of the likelihood that a given question will be selected (or not selected) to be included in a given survey.

In step 204, the questions are stored in the database. For example, questions may be stored in questions database 102, which may be accessible through a server or other computing platform within an organization administering surveys. In step 206, questions to be included in surveys are dynamically selected from the database using the selection probabilities. The surveys are presented to a plurality of different individuals, and the questions are selected such that different individuals are presented with different sets of questions. For example, a patient quality survey given to two patients of a given facility may include the same categories of questions but different questions within each category based on the selection probabilities. In step 208, statistics are generated based on survey results and the selection probabilities are updated based on the statistics. For example, with statistical measures, such as the mean and variance of answers for a given question may be generated. The statistical measures and prior weights can be used to re-weight questions each time results from a survey are obtained. An exemplary algorithm for re-weighting questions will be described in detail below.

Figure 3:
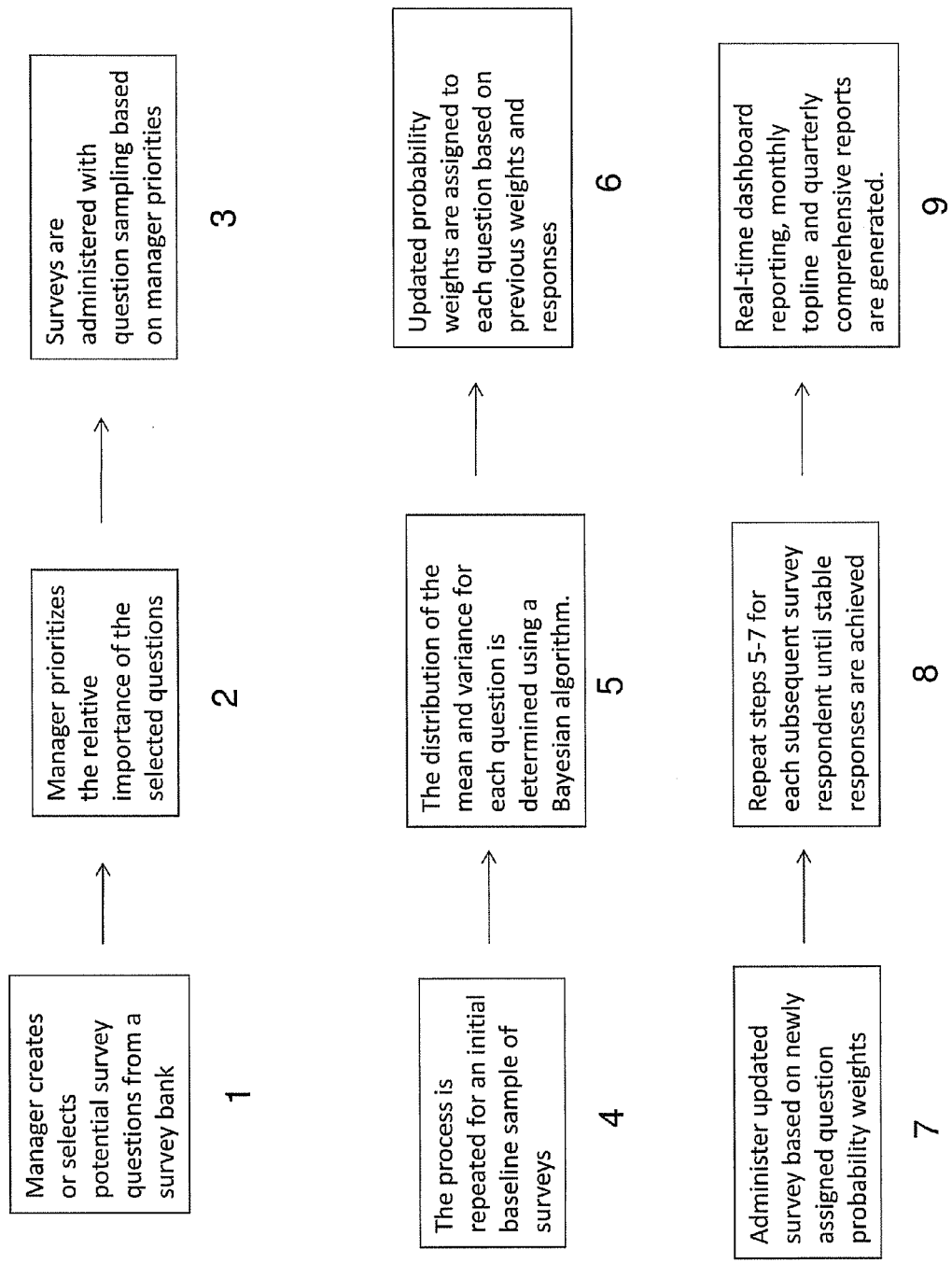
FIG. 3 is a flow diagram illustrating exemplary steps for administering a survey using dynamically-selected questions according to an embodiment of the subject matter described herein.

FIG. 3 is a flow diagram illustrating in more detail steps for survey administration and updating. Referring to FIG. 3, in step 1, a manager selects potential categories of questions and individual questions within each category. In step 2 the manager assigns a priority score to each of the questions indicating the relative weight to be assigned to each question. The manager may also assign relative weights to the categories in step 2. This allows the manager to prioritize the issues most important to the manager and recognizes the limitation that individual patients cannot be realistically expected to answer every question in a long survey. Questions may be drawn from an item bank that assesses key dimensions of the patient experience in actionable detail. The item bank may be customizable so that managers may add their own questions that address issues which may be unique to the managers' business environment (healthcare, retail, etc.). For example, categories and questions for healthcare will be presented below. The manager or administrator may add, delete, or replace questions in the database or item bank. For example, if a manager decides that a new question is important, the manager may add the new question to the database and assign a priority to the new question so that the new question will be potentially selected in subsequent surveys.

In step 3, surveys are administered to patients with questions presented based on sampling priorities derived from the priorities or weights assigned by the manager. In step 4, the process of administering surveys where the questions are sampled based on the priorities is repeated for a baseline number of respondents. In one implementation, 50 respondents were used as the baseline. In step 5, summary statistics are calculated for each question. The questions may be presented so that a user is required to respond with a numeric answer or an answer that can be converted into a number so that the statistics can be calculated. For example, the respondent may be required to indicate a position on a scale that indicates the degree to which the respondent strongly agrees or strongly disagrees with a statement presented in the survey. The position indicated by the user may be converted into a number and used to calculate statistics. Examples of statistics that may be calculated include, for each question, the mean, variance, and variance of the mean. In step 5, the distribution of the mean and the variance of the mean for each question are determined. In step 6, a statistical algorithm is used to generate updated probability weights for each question based on previous weights and responses. The terms "probability weights" and "selection probabilities" are used interchangeably herein. In one implementation, the statistical algorithm is a Bayesian algorithm. However, other statistical algorithms can be used without departing from the scope of the subject matter described herein. For example, classical statistics may be used to calculate the mean and the variance of the mean, which can be used to update the selection probabilities.

The statistical algorithm maximizes the efficiency of the survey process according to manager priorities and the distribution of prior responses. This process helps ensure that managers will receive statistically-valid performance data in the shortest time period possible. By prioritizing questions, the process limits the response burden for individual patients thus leading to significantly higher response rates than traditional surveys.

In step 7, a new survey is generated to the next patient based on the updated question probability weights. Steps 5 through 7 may be repeated in real time for each subsequent survey (step 8). Real time dashboard reporting and periodic pipeline and comprehensive reports may be generated (step 9).

Although the example described in FIG. 3 of developing and implementing surveys using an item bank is for quality of healthcare, the subject matter described herein can be used to solicit user or customer feedback or as a means for developing surveys in other settings, such as employee culture or satisfaction surveys not limited to traditional customer/consumer relationships Advantages of such a system include, without limitation, a customizable user interface (described below), real time tracking of survey data, a novel statistical algorithm that generates a unique survey for each respondent, which maximizes efficiency and statistical validity of the survey process.

FIG. 4A illustrates an example of how a manager assigns priorities to questions and categories as illustrated in step 2 in FIG. 3. Referring to FIG. 4A, a manager may assign 100 points across all categories (k) based on their priorities to the manager. In this example, there are three categories, A, B, and C and five questions in each category. However, there is no limit to the number of potential categories or questions. In block 400, no weights are assigned to the categories. In block 402, the manager has assigned weights to the categories, indicating that category B is the most important with a 60% rating followed by category A with a 30% rating and category C with a 10% rating.

FIG. 4B illustrates the assignment of priorities to questions within each category. In block 404, the priorities are not assigned to the individual questions. In block 406, the manager has assigned a total of 100 points to each question (j) within each category based on the priorities of the questions to the manager. The manager may also add questions or replace questions in each category.

FIG. 4C illustrates the calculation of sampling priorities for each question. In the illustrated example, the selection probability weight for each question is calculated by the following equation:

$$\text{Selection probability weight} = \text{category weight}(j) \times \text{question weight}(k)$$

This equation may be used to initially assign selection probabilities to questions. After initial assignment, selection probabilities may be updated based on responses and current weight, as will be described in more detail below. Block 408 shows the questions and the categories with their assigned weights. Block 410 illustrates the calculation of the selection priorities for each question. The sum of the selection probability weights for all questions will total to 1.

Figure 4D:
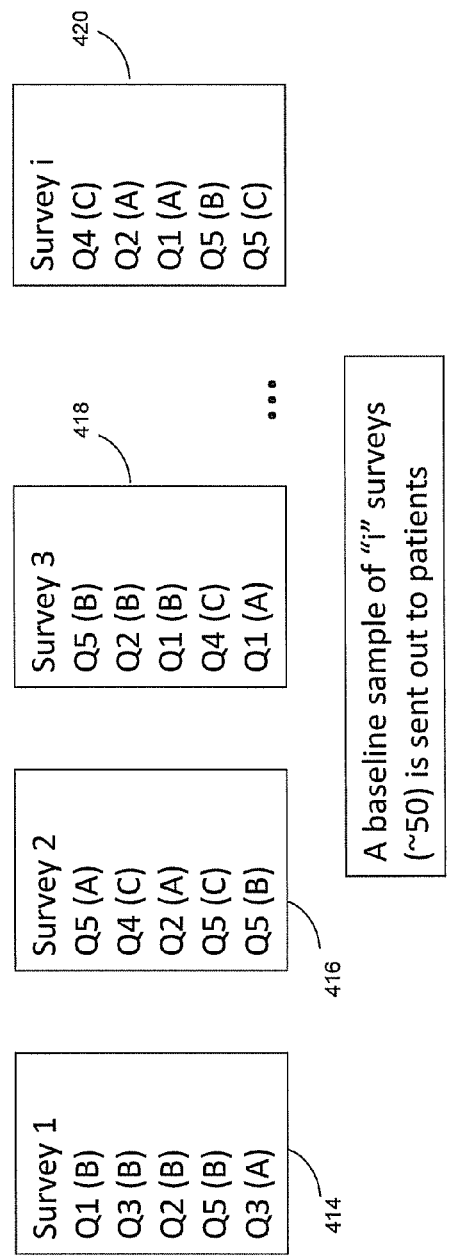
FIG. 4D is a diagram illustrating the generation of surveys using the selection probabilities according to an embodiment of the subject matter described herein.

FIG. 4D illustrates the selection of questions for individual surveys based on the sampling priorities. More particularly, block 412 indicates the selection probabilities for the questions. Blocks 414, 416, 418, and 420 illustrate that surveys presented to different individuals may have different questions based on the selection probabilities. For example, survey 414 includes question 1 from category 1, but survey 416 includes question 5 and not question 1. As an example of how the selection probabilities are used, the probability weight of 0.24 for question 1 in category B means that question 1 will statistically be asked 24% of the time or in 24% of the surveys.

According to an aspect of the subject matter described herein, question selection probabilities are automatically updated based on the current weight and previous answers to the same question. In one exemplary implementation, a metric of the variability of the answers to a given question may be used to increase or decrease the selection probability for the question for subsequent iterations of the survey generation process. The following pseudo code illustrates an example of how to update question selection probabilities according to an embodiment of the subject matter described herein.

Step 1. Update the Estimate of Mean & Variance of the Individual Question Means Using Bayesian Inference with Gibbs Sampler Variable Definitions:
Mu: estimate of population mean as determined by algorithm
Tau: estimate of population variance as determined by algorithm
Nu: 1st parameter in the distribution of sigma
Sigma: 2nd parameter in the distribution of sigma
Sigma2: updated sigma used in updating mu & tau
Specify priors for the distribution of theta, mu, tau, nu, sigma, sigma2
Specify sample size for Gibbs sampler
Sample size=1000
For each question in the survey
   Initialize arrays for mu, tau, nu, sigma and sigma2
   For 1 to sample size
   if previous sigma
     previous sigma=initial sigma
   if previous sigma 2
     previous sigma 2=initial sigma 2
     draws=number of times this question has been draw
     mu=(mu initial/tau initial+draws*mean response value/previous sigma 2)/(1/tau initial+draws/previous sigma 2)
     tau=1/(1/tau initial)+(draws/previous sigma)
     nu=nu initial+draws
     theta=generate random value that conforms to gaussian distribution using tau ^0.5+mu
     if draws>=1
       sum of squares=sum(response value−theta)^2 else
       sum of squares=sigma initial
     sigma=1/nu*(nu*sigma+sum of squares)
     gamma random value=generate random value that conforms to gamma distribution using nu/2 and sigma/2
     sigma 2=(1/gamma random value)
     previous sigma=sigma
     previous sigma 2=sigma 2
     store updated values in mu, tau, nu, sigma, sigma 2
Calculate arithmetic mean of the values of mu, tau, nu, sigma, sigma 2, store in arrays for specific question
The individual question score is the mean of mu, which is an estimate of the mean of the population mean for each question Step 2. Individual Question Probability Weights are Updated Using "Exponential Smoothing" Based on Previous Weights and the Tau Values Calculated Above
New question weight=gamma*(old question weight)+(1−gamma)*(question tau/max question variance on that particular round)

Figure 5:
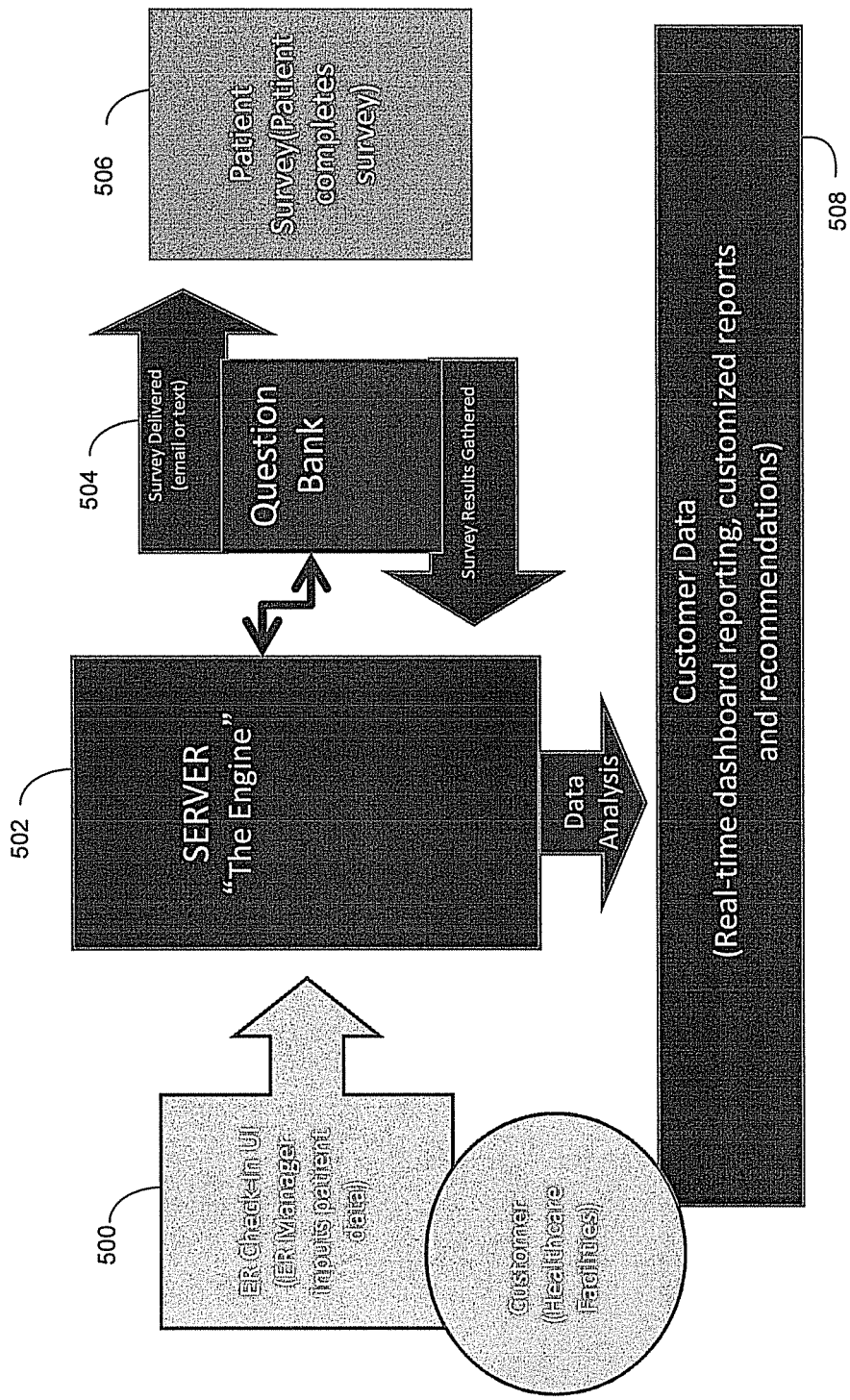
FIG. 5 is a block diagram of a system for administering surveys in a healthcare environment using dynamically selected questions according to an embodiments of the subject matter described herein.

FIG. 4E illustrates question weightings for an initial sample of surveys, numbered 1-50 and the question weightings for a next survey, survey 51. In this hypothetical scenario, the weights are adjusted for survey number 51. Question 1 in category B was initially the highest priority question. Among initial respondents the variance of the response was low, indicating a high degree of confidence in the true answer. Therefore, the question was de-weighted from 0.24 to 0.05. In contrast, question 2 in category B initially received a moderate weighting of 0.12. In this scenario, the answers among initial respondents were highly variable. Since this question is important and the true answer is still unclear, the weighting for this question is increased significantly from 0.12 to 0.25. By dynamically re-weighting questions, important questions with highly variable answers can be increased in selection probability while unimportant questions and/or questions whose variability does not change may be de-weighted. The process of updating the distribution of the mean and variance of the questions and re-weighting the questions may be repeated for each survey response or groups of survey responses. New surveys may be generated in real time based on the updated question selection probabilities FIG. 5 is a block diagram illustrating an overall framework for generating and administering surveys to obtain feedback from patients in near real time and providing a real time management tool. Referring to FIG. 5, patients may provide their email address and/or cell phone number at the time of registration, as indicated by block 500. The information may be uploaded to a server 502 that generates surveys and performs the analyses described herein. Server 502 may generate surveys from questions stored in question bank 504. Surveys may be delivered to patients using any electronic means, such as email or cell phone within a short time of receiving care. When a patient completes survey 506, the survey results are provided to server 502 and server 502 generates data analysis 508. The results may also be used to update survey question selection probabilities for subsequent rounds.

As stated above, the subject matter described herein may include a graphical user interface that facilitates survey generation. The following description and associated figures illustrate an exemplary interface that may be presented by the system illustrated in FIG. 1.

Figure 6A:
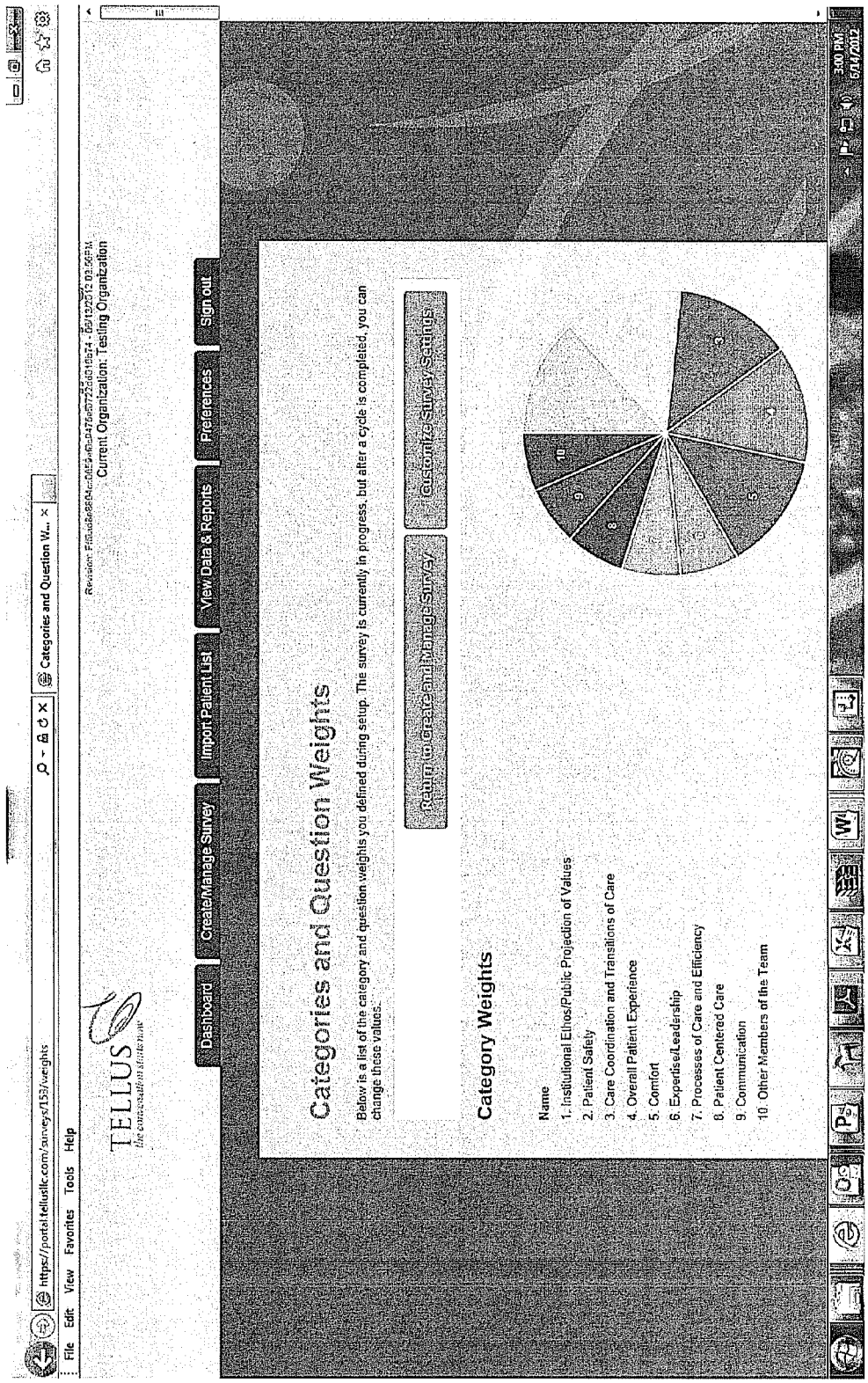
FIG. 6A is a computer screen shot of an exemplary user interface for displaying category weights to an administrator according to an embodiment of the subject matter described herein.
Figure 6B:
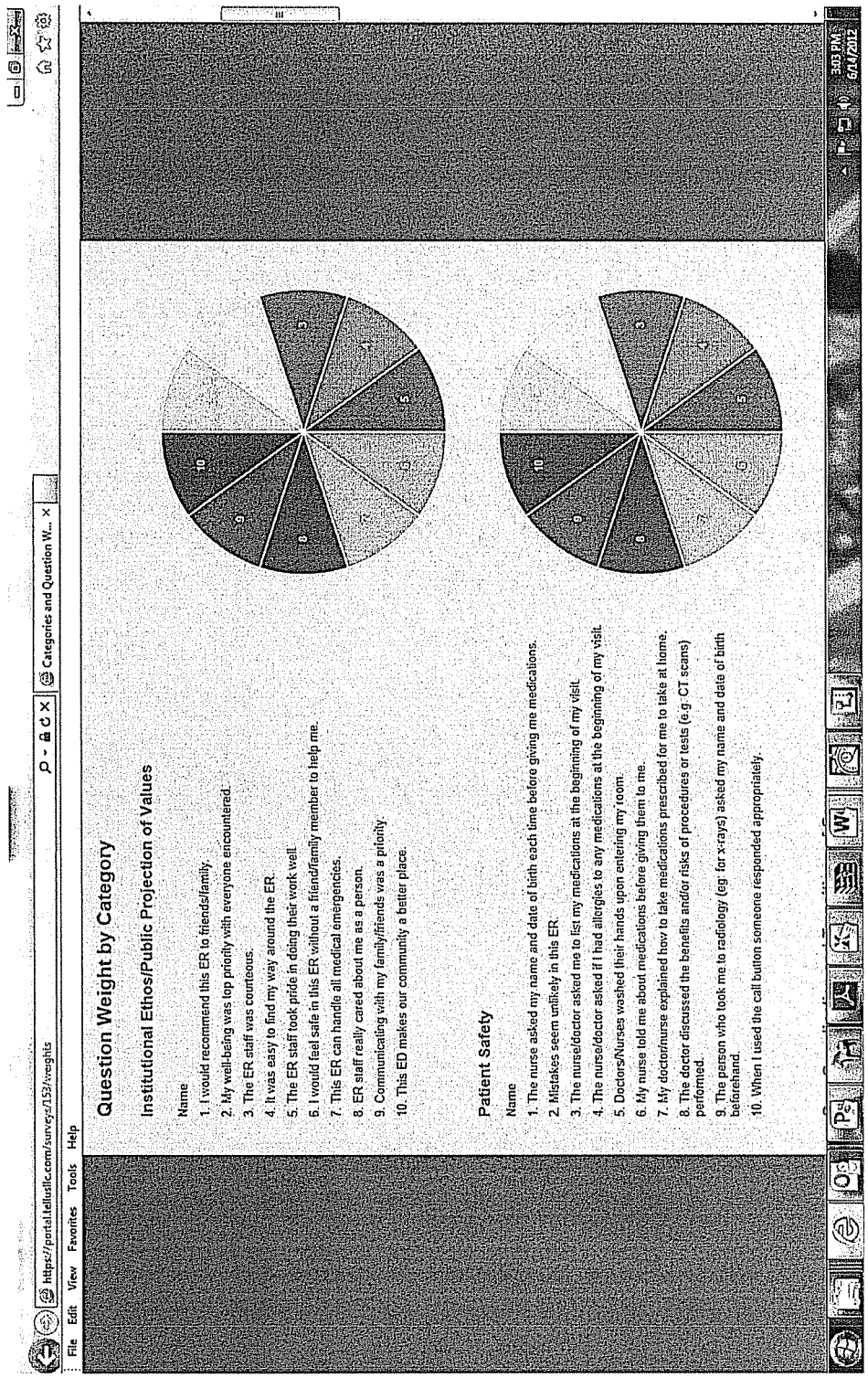
FIG. 6B illustrates an exemplary computer screen shot of an interface that may be displayed by scrolling down from the interface in FIG. 6A.

FIG. 6A is a computer screen shot of a graphical user interface for displaying categories and corresponding category weights according to an embodiment of the subject matter described herein. In FIG. 6A, a pie chart is shown displaying different category weights for each category in a healthcare survey. FIG. 6B is computer screen shot of an interface that may be displayed by scrolling down from the interface in FIG. 6A where weights are presented for individual questions within the first two categories. As in FIG. 6A, the weight assigned to each question may be presented graphically to the user in a pie chart format. Additional interfaces such as that illustrated in FIG. 8B may be presented for the questions in the remainder of the categories.

Figure 7A:
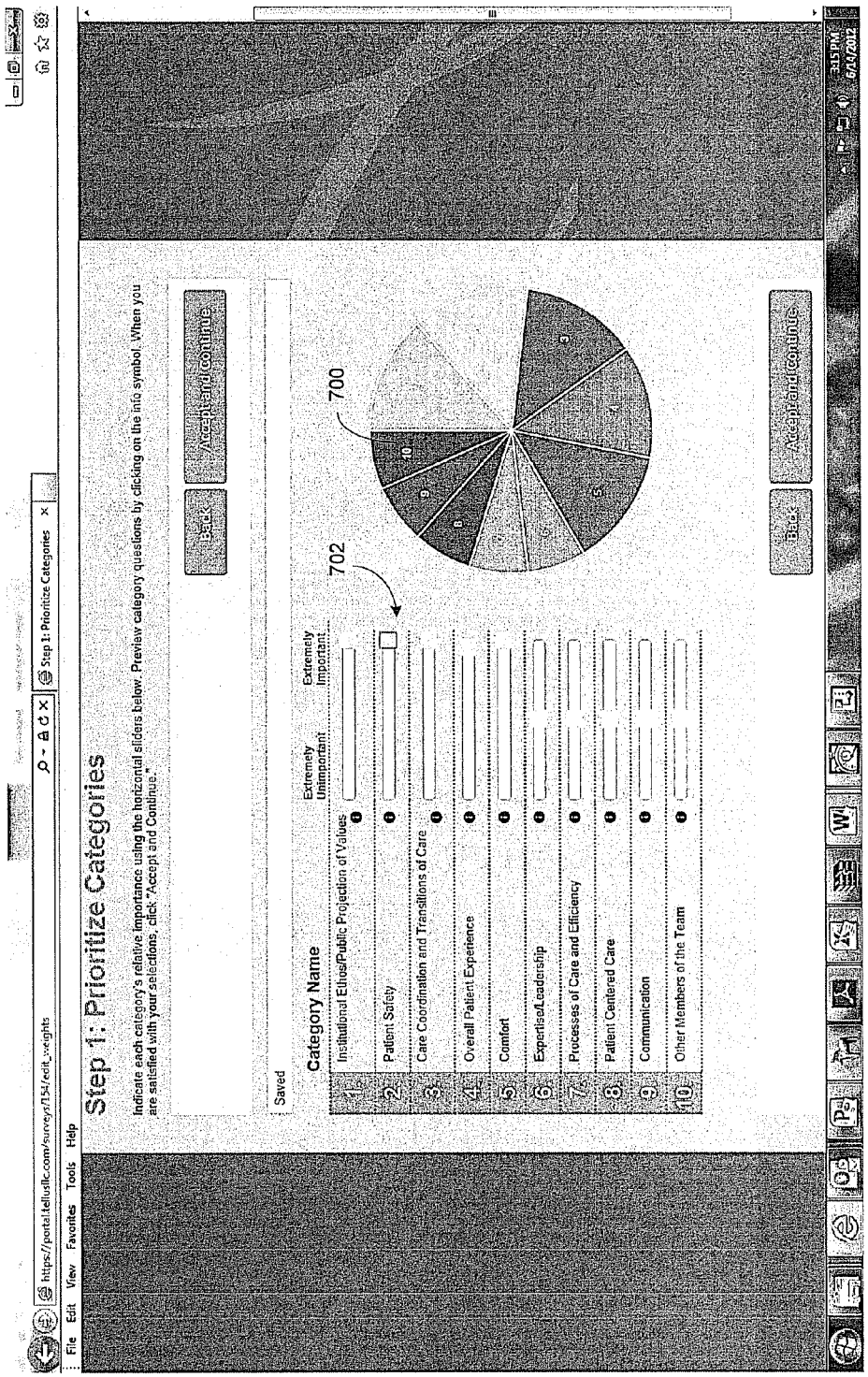
FIG. 7A is a computer screen shot of an interface for manipulating the relative weights assigned to each category according to an embodiment of the subject matter described herein.
Figure 7B:
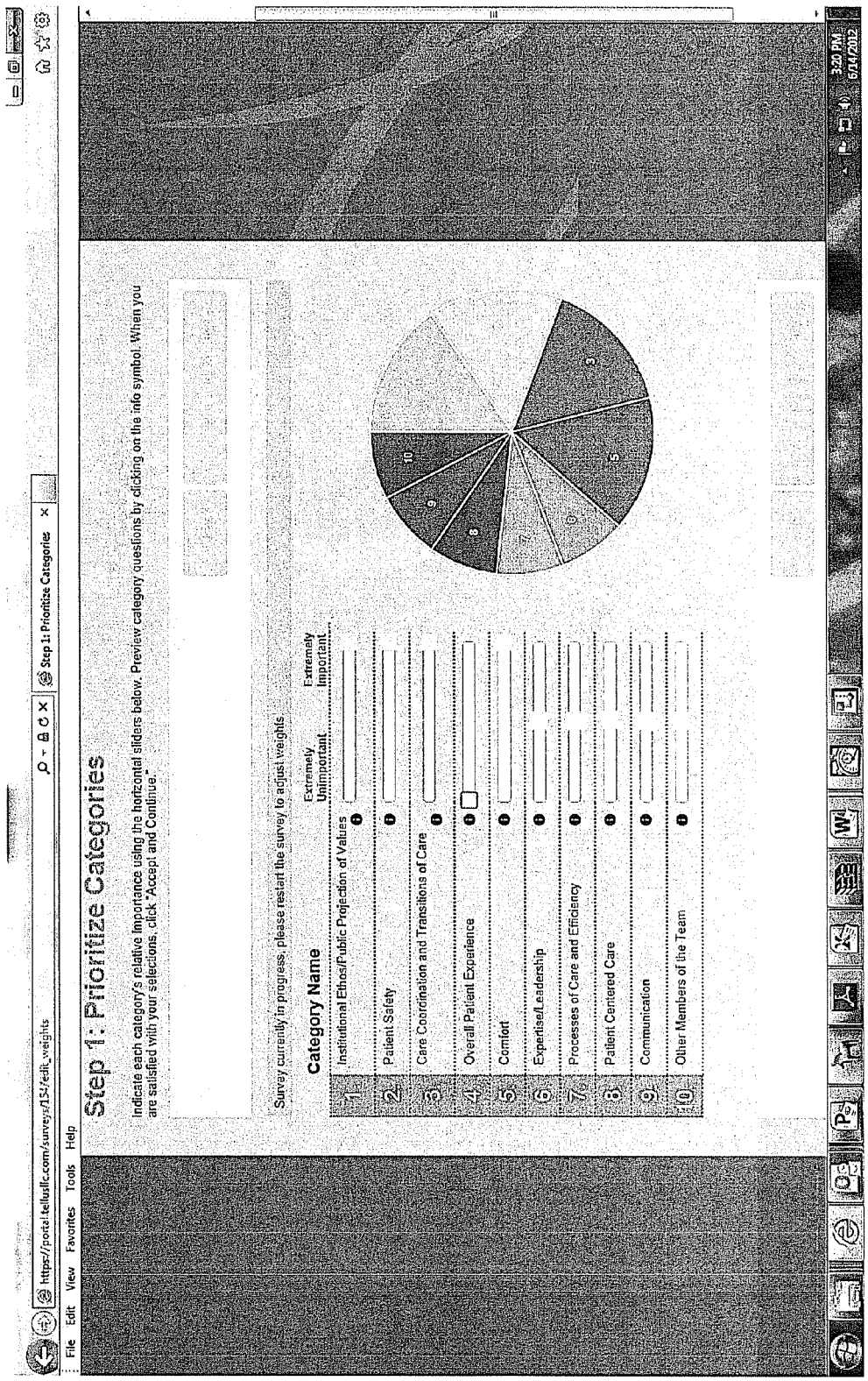
FIG. 7B is a computer screen shot of the interface illustrated in FIG. 7A showing the result of changing the weight of one of the categories according to an embodiment of the subject matter described herein.

According to an aspect of the subject matter described herein, the system illustrated in FIG. 1 presents a convenient graphical user interface to the user that allows the user to easily manipulate the relative weights of the categories and the questions within each category. FIG. 7A illustrates an example of an interface for manipulating the relative weights assigned to each category. Referring to FIG. 7A, a pie chart 700 displays relative weights assigned to each question category is displayed to the user. A slider interface 702 contains a graphical slider for each category that when manipulated changes the relative weight assigned to the category. As illustrated in FIG. 7B, when the slider corresponding to the overall patient experience category is changed from extremely important to extremely unimportant, its resulting portion of the pie chart goes to zero and the relative weights assigned to the remaining categories increase proportionately with their current weights so that the total weight assigned to all of the categories is equal to one hundred percent.

Figure 7C:
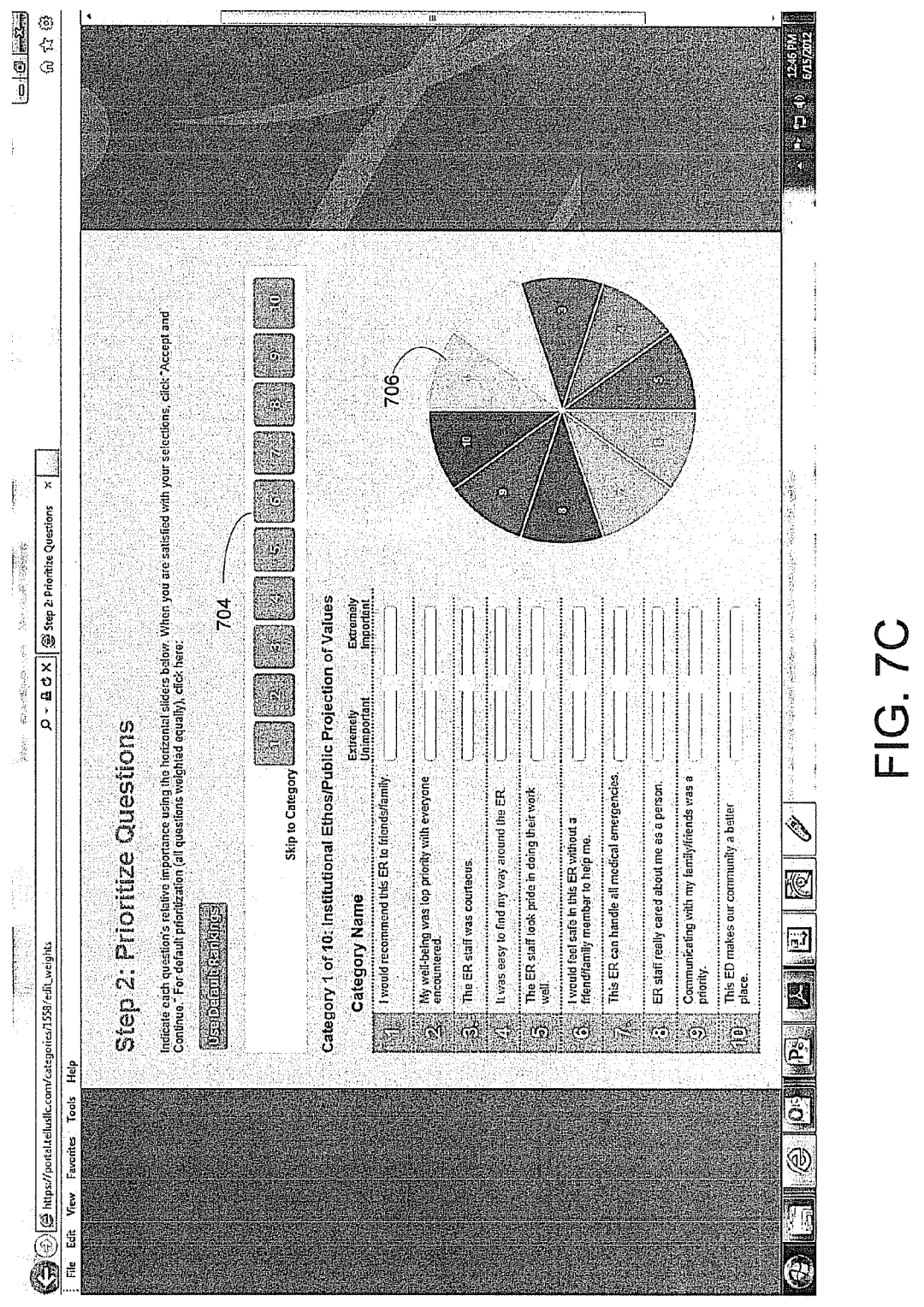
Figure 7D:
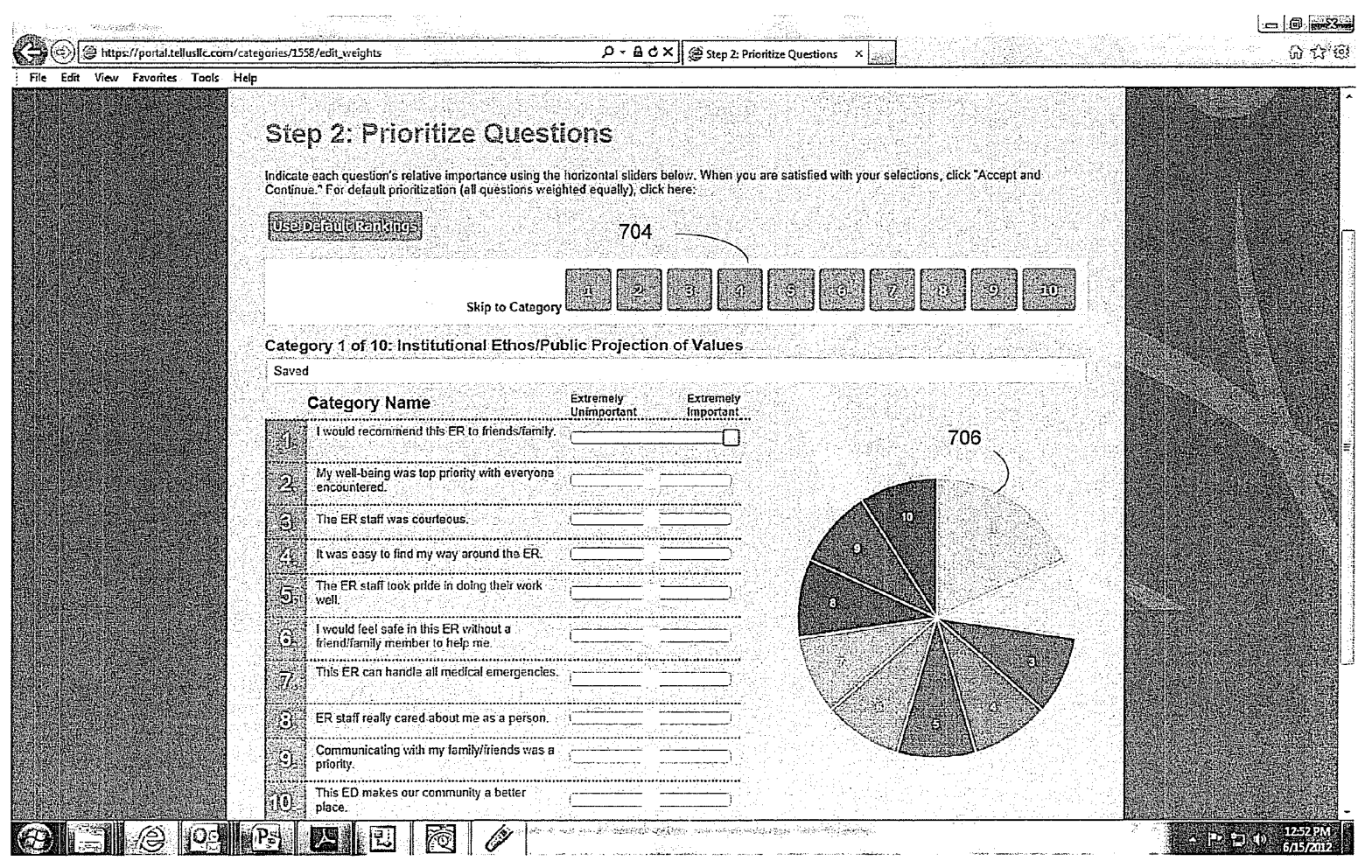

Similar to the interface illustrated in FIGS. 7A and 7B for assigning weights to categories, FIGS. 7C and 7D are computer screen shots of exemplary graphical user interface for assigning weights to questions within each category. In FIG. 7C, buttons 704 represent the various categories. By selecting one of buttons 704, the administrator can display a pie chart 706 that illustrates the relative weights assigned to the questions for the selected category. In the illustrated example, category 1 is selected and pie chart 706 displays the relative weights assigned to the questions in category 1. To illustrate the functionality of the interface illustrated in FIG. 7C, before modification by the administrator, each of the questions is assigned the same relative weight. Since there are ten questions with equal weight, each question would be assigned a weight of 10. As illustrated in FIG. 7D, when the weight assigned to question number 1 is doubled to 20, the corresponding share of the pie for question number 1 increases to 20% of the overall pie. In addition, the weights assigned to the other questions automatically decrease proportionately to the remaining total percentage. For example, if the weight for question 1 is increased to 20, 80 points are available for the remaining nine questions, resulting in each question being assigned a weight of 8.89.

Figure 8A:
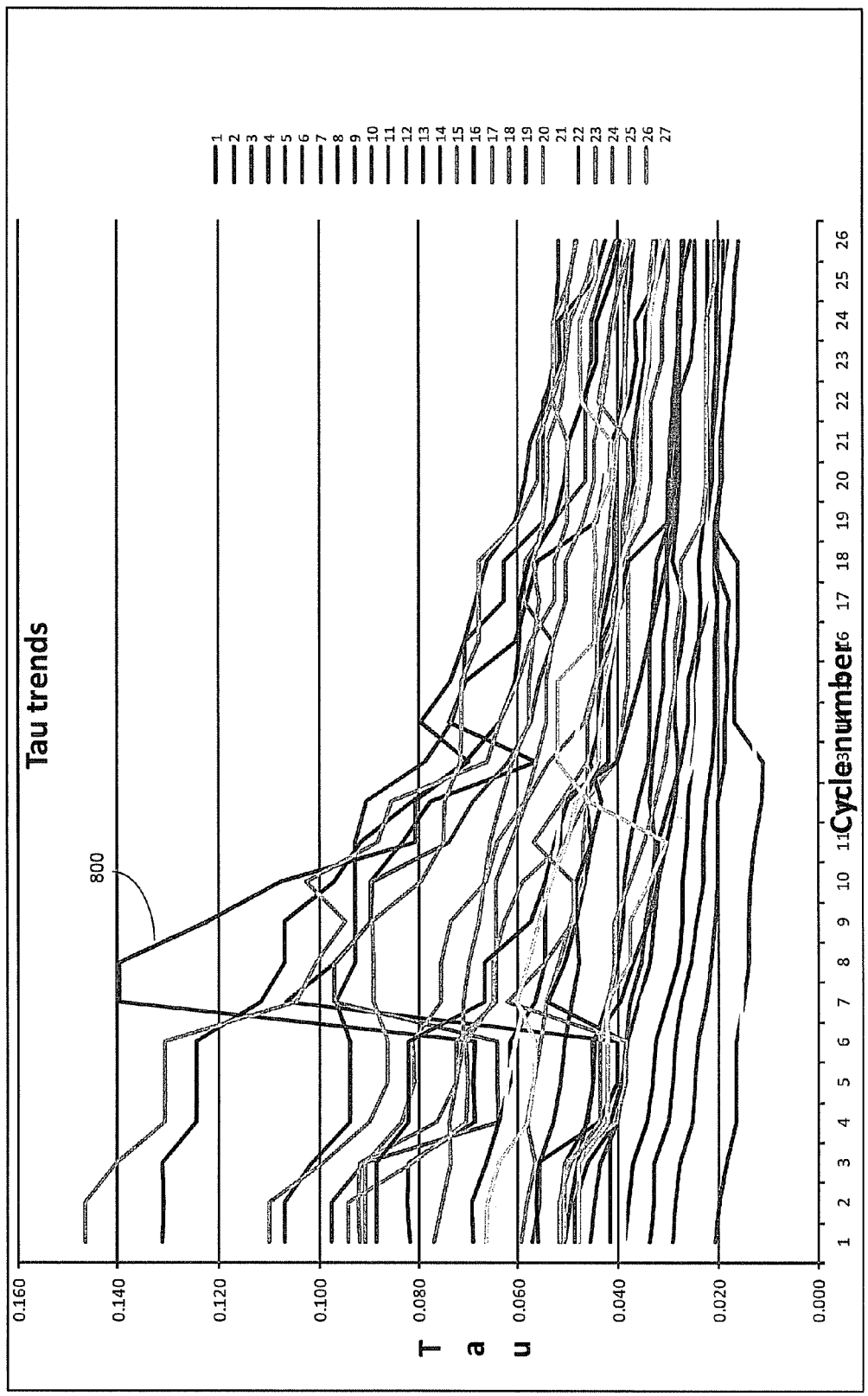
FIG. 8A is a graph of Tau trends of answers to individual questions according to an embodiment of the subject matter described herein.
Figure 8B:
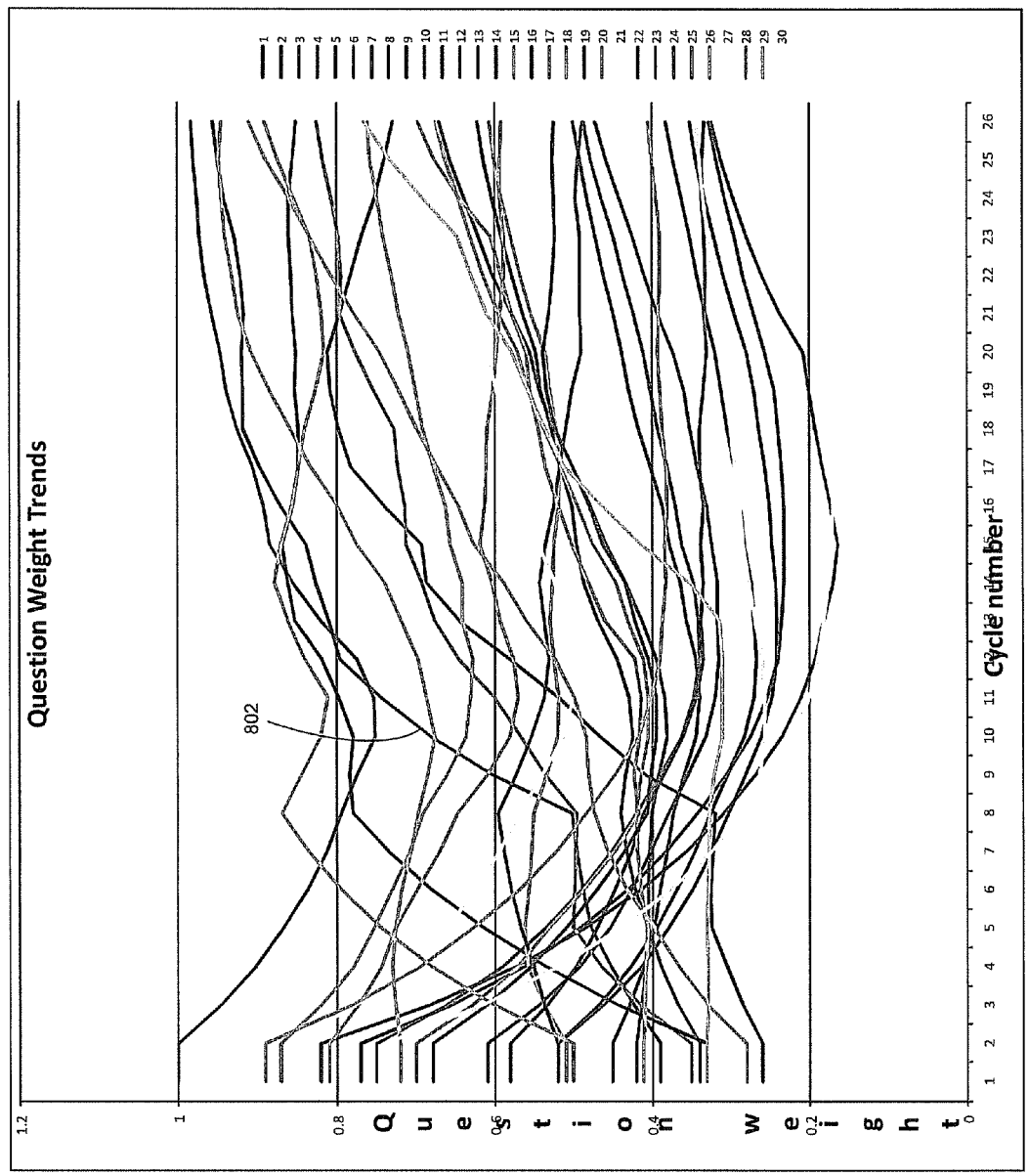
FIG. 8B is a graph of question probability weight trends corresponding to the Tau trends illustrated in FIG. 8A.

As stated above, selection probability weights for questions may be dynamically updated based on current answers and statistics associated with previous answers. FIG. 8A is a graph of Tau trends of answers to individual questions and FIG. 8B is a graph of question probability weight trends corresponding to the Tau trends illustrated in FIG. 8A. The data in FIGS. 8A and 8B was obtained from answers to patient surveys in a healthcare facility. Tau is a statistical measure of the variability around the mean. As illustrated by the curve for question 10, indicated by reference number 800, the variability of answers for a question may initially increase, level off, then may decrease (as the mean becomes more certain). In FIG. 8B, reference numeral 802 illustrates the corresponding change in question weighting for question 10, the probability weighting assigned to question 10 increases during the period of high answer variability and then levels off when the variability in the answers decreases.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for dynamically selecting questions to be presented in a survey, the method comprising:
    at a computing platform including at least one processor:
        providing for assignment of priorities to potential survey questions;
        determining a selection probability for each question based on the assigned priorities;
        storing questions in a database embodied in a non-transitory computer readable medium; and
        dynamically selecting, from the database and based on the selection probabilities, questions to be included in surveys to be presented to a plurality of individuals such that different individuals are presented with different sets of questions,
        wherein providing for assignment of priorities to the questions includes providing for assignment of priorities to categories and providing for assignment of priorities to individual questions within each category and wherein determining selection probabilities includes calculating the selection probabilities based on the priorities assigned to the categories and on the priorities assigned to the individual questions, wherein the selection probability for each question is calculated by multiplying a category priority weight and an individual question priority weight.

2. The method of claim 1 wherein providing for assignment of priorities to categories includes providing a manipulable graphical depiction of the priorities assigned to the categories.

3. The method of claim 2 wherein the manipulable graphical depiction comprises a slider interface where movement of a slider changes the priority assigned to a category, automatically updates priorities assigned to remaining categories, and visually displays the updated priorities.

4. The method of claim 1 wherein providing for assignment of priorities to the questions includes providing a manipulable graphical depiction of the priorities assigned to the questions.

5. The method of claim 4 wherein the manipulable graphical depiction comprises a slider interface where movement of a slider changes the priority assigned to a question, automatically updates priorities assigned to remaining questions within a category, and visually displays the updated priorities.

6. The method of claim 1 comprising receiving answers to the questions and automatically updating the selection probabilities based on the answers.

7. The method of claim 6 wherein automatically updating the selection probabilities based on the answers includes decreasing the selection probability for a question based on a metric of variability of the answers.

8. The method of claim 6 wherein automatically updating the selection probabilities includes increasing the selection probability for a question increasing the selection probability for a question based on a metric of variability of the answers.

9. The method of claim 1 wherein the questions are directed to one of: finance, politics, public opinion, employee performance, consulting, education, credit card, healthcare, retail, hospitality, or restaurant.

10. A system for dynamically selecting questions to be presented in a survey, the system comprising:
    a computing platform including at least one processor, the computing platform comprising:
        a questions database configured to store a plurality of potential survey questions stored in a non-transitory computer readable medium;
        a priority assignment module for providing for assignment of priorities to the potential survey questions;
        a selection probability determination module for determining a selection probability for each potential survey question based on the assigned selection priorities; and
        a question selection module for dynamically selecting, from the questions database and based on the selection probabilities, questions to be included in the survey to be presented to each of the plurality of individuals such that different individuals are presented with different questions,
    wherein the priority assignment module is configured to provide an interface for an administrator to assign priorities to categories and providing for assignment of priorities to individual questions within each category and wherein determining selection probabilities includes calculating the selection probabilities based on the priorities assigned to the categories and on the priorities assigned to the individual questions, wherein the selection probability for each question is calculated by multiplying a category priority weight and an individual question priority weight.

11. The system of claim 10 wherein the interface comprises a manipulable graphical depiction of the priorities assigned to the categories.

12. The system of claim 11 wherein the manipulable graphical depiction comprises a slider interface where movement of a slider changes the priority assigned to a category, automatically updates priorities assigned to remaining categories, and visually displays the updated priorities.

13. The system of claim 10 wherein the priority assignment module is configured to provide an interface including a manipulable graphical depiction of the priorities assigned to the questions.

14. The system of claim 13 wherein the manipulable graphical depiction comprises a slider interface where movement of a slider changes the priority assigned to a question, automatically updates priorities assigned to remaining questions within a category, and visually displays the updated priorities.

15. The system of claim 10 wherein the selection probability determination module is configured to receive answers to the questions and to automatically update the selection probabilities based on the answers.

16. The system of claim 15 wherein the selection probability determination module is configured to decrease the selection probability for a question based on a metric of variability of answers to the question.

17. The system of claim 15 wherein the selection probability determination module is configured to increase the selection probability for a question based on a metric of variability of answers to the question.

18. The system of claim 10 wherein the questions are directed to finance, politics, public opinion, employee performance, consulting, education, credit card, healthcare, retail, hospitality, or a restaurant.

19. A non-transitory computer readable medium having stored thereon executable instructions that when executed by the processor of a computer control the computer to perform steps comprising:
 providing for assignment of priorities to potential survey questions;
 determining a selection probability for each question based on the assigned priorities;
 storing questions in a database; and
 dynamically selecting, from the database and based on the selection probabilities, questions to be included in surveys to be presented to a plurality of individuals such that different individuals are presented with different sets of questions,
wherein providing for assignment of priorities to the questions includes providing for assignment of priorities to categories and providing for assignment of priorities to individual questions within each category and wherein determining selection probabilities includes calculating the selection probabilities based on the priorities assigned to the categories and on the priorities assigned to the individual questions, wherein the selection probability for each question is calculated by multiplying a category priority weight and an individual question priority weight.

\* \* \* \* \*